United States Patent [19]

Parker

[11] Patent Number: 4,859,240

[45] Date of Patent: * Aug. 22, 1989

[54] DENTAL AMALGAM ALLOY

[75] Inventor: Graham J. Parker, Malvern, Australia

[73] Assignee: Jeffery James Cheetham, Bayswater, Australia

[*] Notice: The portion of the term of this patent subsequent to Aug. 11, 2004 has been disclaimed.

[21] Appl. No.: 58,831

[22] Filed: Jun. 5, 1987

Related U.S. Application Data

[62] Division of Ser. No. 626,722, Jul. 2, 1984, Pat. No. 4,686,082.

[30] Foreign Application Priority Data

Jul. 8, 1983 [AU] Australia .............................. PG0209
Aug. 1, 1983 [AU] Australia .............................. PG0594

[51] Int. Cl.$^4$ .............................................. B22F 1/00
[52] U.S. Cl. ..................................... 75/251; 420/503; 420/504; 420/587; 420/589; 433/228.1

[58] Field of Search ............... 420/503, 504, 587, 589; 75/251; 433/228.1

[56] References Cited

U.S. PATENT DOCUMENTS

| 4,374,085 | 2/1983 | Asgar et al. | 420/470 |
| 4,664,629 | 5/1987 | Chodkowski | 420/503 |
| 4,686,082 | 8/1987 | Parker | 420/503 |

FOREIGN PATENT DOCUMENTS

| 0033628 | 8/1981 | European Pat. Off. | |
| 56-15453 | 4/1981 | Japan | 420/503 |

Primary Examiner—John P. Sheehan
Attorney, Agent, or Firm—William R. Hinds

[57] ABSTRACT

The present invention relates to a dental amalgam alloy comprising by weight, as alloying ingredients, from about 30 to 70% silver, from about 20 to 35% tin, from about 10 to 30% cooper, from 0 to about 5% indium, from 0 to about 1% zinc and from about 0.01 to 2% of a Group VIII metal selected from the group consisting of platinum, rhodium, iridium and ruthenium.

5 Claims, No Drawings

DENTAL AMALGAM ALLOY

This is a division of application Ser. No. 626,722, filed July 2, 1984, now U.S. Pat. No. 4,686,082.

The present invention relates to dental amalgam alloys. Dental alloys are typically silver based alloys which can be admixed in particulate form with mercury to produce an amalgam which is initially soft and pliable but which sets to a hard mass after a time. Thus, when fresh amalgam is placed in a tooth cavity it can be worked by the dentist to completely fill the cavity and to have an external configuration consistent with that of the remainder of the tooth.

Conveniently, silver based dental alloys contain a major proportion of silver such as 60% or more of silver by weight. The balance may be made up of a number of elements but is made up chiefly of tin and copper. However, the price of silver has increased in recent times and thus it is desirable to reduce the amount of silver in a dental amalgam alloy to lower the cost of it. On the other hand, the dental amalgam alloys must exhibit satisfactory properties both clinically and metallurgically.

It has now been found that the properties of a low silver alloy containing silver, copper and tin can be improved by the incorporation therein of metals from Group VIII of the Periodic Table which are platinum, rhodium, iridium and ruthenium, particularly platinum.

European Pat. No. 33628 and corresponding Australian Application No. 66702/81 in the name of Macrodent S. A. refer to dental amalgam alloys which may contain platinum. However, the only disclosure of a means of incorporating the platinum is by superficially covering particles with platinum. No particular benefit is attributed to the use of platinum and no platinum containing example is disclosed. This patent merely states that the alloy may contain up to 3% total of one, another, or any combination of gold, platinum or palladium. However, there is no disclosure of the use of platinum as an alloying ingredient. U.S. Pat. No. 4,374,085 discloses a dental amalgam alloy which may contain up to 2% ruthenium. However, the main thrust of this invention is the inclusion in the alloy of from 0.05 to 0.95% palladium. One example discloses the use of 0.5% ruthenium. No particular benefit is attributed to the use of ruthenium.

In accordance with the present disclosure there is provided a dental amalgam alloy comprising by weight, as alloying ingredients, from about 30 to 70% silver, from about 20 to 35% tin, from about 10 to 30% copper, from 0 to about 5% indium, from 0 to about 1% zinc and from about 0.01 to 2% of a Group VIII metal selected from the group consisting of platinum, rhodium, iridium and ruthenium.

The alloy may also contain incidental minor amounts of impurities.

Preferably, the alloy comprises by weight from about 35 to 55% silver, from about 20 to 30% tin, from about 15 to 30% copper, from about 0.1 to 5% indium and from about 0.01 to 2% of a Group VIII metal selected from the group consisting of platinum, rhodium, iridium and ruthenium. Preferably, when zinc is present in the alloy it is present in an amount of about 0.5% by weight of the alloy.

It is preferred that the silver content of the alloy be at least 30% by weight of the alloy to reduce corrosion problems. On the other hand, the use of higher amounts of silver increases the cost of the alloy. It has been found that particularly satisfactory results are obtained with an alloy in accordance with the present invention which contains from about 40 to 50% by weight of silver.

Further, the addition of small amounts of certain Group VIII metals is found to improve various properties of the alloy such as compressive strength, static creep and/or diametral tensile strength. Further, the incorporation of the Group VIII metals produces an alloy which, in the resultant amalgam, leads to a low gamma 2 content. Gamma 2 is desirably kept low since this component of an amalgam is the weakest and the most corrodible component thereof.

It has been found that the optimum improvement with the use of these Group VIII metals is obtained with the addition of amounts towards the lower end of the range set out above.

The Group VIII metals concerned are extremely expensive so any improvement obtained with the addition of larger amounts of these Group VIII metals has to be balanced against the increase in overall cost of the alloy.

Preferably, the Group VIII metal is incorporated in the alloy in an amount in the range by weight from about 0.03% to 1%, more preferably from about 0.03% to 0.1%.

The preferred Group VIII metal is platinum.

Further, it has been found that the incorporation in the alloy of a minor amount of indium in addition to the Group VIII metal enhances the obtained improvement in properties. Preferably, the indium is used in an amount by weight from about 0.5 to 3% of the alloy.

The alloy is used in the form of discrete particles which are preferably spherical.

To form spherical particles, the alloy may be formed into a melt. The melt is then atomised in known manner to form discrete liquid droplets which solidify to form solid spherical particles.

In the particles of the present invention the alloying ingredients are substantially uniformly distributed through each particle although there may be minor variations between the cores of particles and the peripheries thereof. These variable compositions are known as gradient compositions.

The spherical particles may have particle sizes in the range from 1 to 100 microns.

Preferably, the spherical particles have particle sizes in the range from 2 to 55 microns with the majority of the particles being less than 35 microns in particle size. Typically, the majority of the particles have particles sizes in the range from 5 to 30 microns. Further, it has been found that by using alloys in accordance with the present invention the amount of mercury required for satisfactory amalgamation is less than that required for a comparable silver-tin-copper alloy. In particular, satisfactory amalgams are obtained using alloys of the present invention with a weight ratio of alloy to mercury of 10:8.5 or less. In particular satisfactory amalgams have been obtained with alloy to mercury ratios of 10:8 and even as low as 10:7.3. The use of lesser amounts of mercury is advantageous in that there is then less matrix between the alloy particles and thus less possibility of the formation of gamma 2 phase.

In accordance with the invention as claimed herein, there is provided a particulate dental amalgam alloy consisting of spherical particles formed of a dental amalgam alloy consisting essentially of, as alloying ingredients substantially uniformly distributed through each particle, from about 40 to 50% by weight silver, from about 20 to 30% by weight tin, from about 15 to 30% by weight copper, from 0 to about 1% by weight zinc and from about 0.03 to 0.5% by weight platinum, said particles having a particle size in the range from 1 to 55 microns with a majority of the particles being less than 35 microns in particle size.

Also in accordance with the invention as claimed herein, there is provided a particulate dental amalgam alloy consisting of spherical particles formed of a dental amalgam alloy consisting essentially of, as alloying ingredients substantially uniformly distributed through each particle, from about 40 to 50% by weight silver, from about 20 to 30% by weight tin, from about 15 to 30% by weight copper, and from about 0.03 to 0.1% by weight platinum, said particles having a particle size in the range from 1 to 55 microns with a majority of the particles being less than 35 microns in particle size.

The present invention will now be described with reference to the following Examples.

The following two comparative examples set out the results obtained with alloys containing silver, tin and copper but no platinum.

COMPARATIVE EXAMPLE 1

An alloy formulation consisting of by weight 46% silver, 28% tin, 24% copper and 2% indium was formed into a melt. The melt was atomised in known manner to form solid spherical alloy particles.

The obtained spherical alloy particles were acid treated in 5% by volume hydrochloric acid and annealed at 180° C. for 1 hour. An amalgam was made with mercury (alloy:mercury ratio 10:9. by weight) and specimens of the amalgam were tested according to the American Dental Association Specification for Dental Alloys.

The results obtained were as follows:

| 30 minute compressive strength | 18,650 p.s.i. |
| 60 minute compressive strength | 30,680 p.s.i. |
| 24 hour compressive strength | 55,920 p.s.i. |
| 7 day compressive strength | 64,600 p.s.i. |
| 1 hour diametral tensile strength | 3,430 p.s.i. |
| 7 day static creep | 0.15 percent |
| Dimensional Change | +0.1 percent |
| Gamma 2 presence | not detected. |

COMPARATIVE EXAMPLE 2

An alloy formulation consisting by weight of 47% silver, 28% tin and 25% copper was made by the technique of comparative Example 1. An amalgam was made with mercury (alloy:mercury ratio 10:9 by weight) and specimens were tested as in Comparative Example 1.

The results obtained were as follows:

| 30 minute compressive strength | 16,500 p.s.i. |
| 60 minute compressive strength | 29,600 p.s.i. |
| 24 hour compressive strength | 55,500 p.s.i. |
| 7 day compressive strength | 67,200 p.s.i. |
| 1 hour diametral tensile strength | 3,274 p.s.i. |
| 7 day static creep | 0.15 percent |
| Dimensional Change | +0.1 percent |
| Gamma 2 presence | not detected |

The following examples set out the results obtained with various alloys in accordance with the present invention which contain silver, tin, copper, platinum and in some instances indium.

EXAMPLE 1

An alloy formulation consisting of by weight 47% silver, 28% tin, 24% copper, 1% platinum was formed into a melt. The melt was atomised in known manner to form solid spherical alloy particles.

The obtained spherical alloy particles were acid treated in 5% by volume hydrochloric acid and annealed at 180° C. for 1 hour. An amalgam was made with mercury (alloy:mercury ratio 10:8 by weight) and specimens of the amalgam were tested according to the American Dental Association Specification for Dental Alloys.

The results obtained were as follows:

| 30 minute compressive strength | 21,600 p.s.i. |
| 60 minute compressive strength | 26,500 p.s.i. |
| 24 hour compressive strength | 61,000 p.s.i. |
| 7 day compressive strength | 74,000 p.s.i. |
| 1 hour diametral tensile strength | 3,395 p.s.i. |
| 7 day static creep | 0.07 percent |
| Dimensional change | +0.1 percent |
| Gamma 2 presence | not detected |

EXAMPLE 2

An alloy containing by weight 47% silver, 24.5% copper, 28% tin and 0.5% platinum was made by the technique of Example 1.

The obtained alloy was formed into an amalgam and tested as described in Example 1. The results obtained were as follows:

| 30 minute compressive strength | 21,500 p.s.i. |
| 60 minute compressive strength | 37,000 p.s.i. |
| 24 hour compressive strength | 63,250 p.s.i. |
| 7 day compressive strength | 75,000 p.s.i. |
| 1 hour diametral tensile strength | 4,712 p.s.i. |
| 7 day static creep | 0.05 percent |
| Dimensional Change | +0.1 percent |
| Gamma 2 presence | not detected |

EXAMPLE 3

An alloy containing by weight 47% silver, 24.95% copper, 28% tin and 0.05% platinum was made by the technique of Example 1. The obtained alloy was formed into an amalgam and tested as described in Example 1. The results obtained were as follows:

| 30 minute compressive strength | 23,600 p.s.i. |
| 60 minute compressive strength | 46,500 p.s.i. |
| 24 hour compressive strength | 69,500 p.s.i. |
| 7 day compressive strength | 77,400 p.s.i. |
| 1 hour diametral tensile strength | 5,225 p.s.i. |
| 7 day static creep | 0.04 percent |
| Dimensional Change | +0.1 percent |
| Gamma 2 presence | not detected |

EXAMPLE 4

An alloy containing by weight 47% silver, 24.97% copper, 28% tin, and 0.03% platinum was made by the technique of Example 1. The obtained alloy was formed into an amalgam and tested as described in Example 1. The results obtained were as follows:

| | |
|---|---|
| 30 minute compressive strength | 18,600 p.s.i. |
| 60 minute compressive strength | 39,500 p.s.i. |
| 24 hour compressive strength | 66,500 p.s.i. |
| 7 day compressive strength | 69,800 p.s.i. |
| 1 hour diametral tensile strength | 5,275 p.s.i. |
| 7 day static creep | 0.09 percent |
| Dimensional Change | +0.1 percent |
| Gamma 2 presence | not detected |

From Examples 1 to 4, it appears that the optimum amount of platinum is between about 0.05 and 0.1%. Below 0.05% platinum the properties of the alloy are not as good and above about 0.1% platinum the properties are also slightly less good than in the apparent optimum range.

EXAMPLE 5

An alloy containing by weight 46% silver, 23% copper, 28% tin, 2% indium and 1% platinum was made by the technique of Example 1. The obtained alloy was formed into an amalgam and tested as described in Example 1.

The results obtained were as follows:

| | |
|---|---|
| 30 minute compressive strength | 20,650 p.s.i. |
| 60 minute compressive strength | 35,600 p.s.i. |
| 24 hour compressive strength | 68,900 p.s.i. |
| 7 day compressive strength | 75,300 p.s.i. |
| 1 hour diametral tensile strength | 4,073 p.s.i. |
| 7 day static creep | 0.08 percent |
| Dimensional Change | +0.1 percent |
| Gamma 2 presence | not detected |

EXAMPLE 6

An alloy containing by weight 46% silver, 23.9% copper, 28% tin, 2% indium and 0.1% platinum was made by the technique of Example 1. The obtained alloy was formed into an amalgam and tested as described in Example 1.

The results obtained were as follows:

| | |
|---|---|
| 30 minute compressive strength | 22,500 p.s.i. |
| 60 minute compressive strength | 46,500 p.s.i. |
| 24 hour compressive strength | 68,000 p.s.i. |
| 7 day compressive strength | 78,000 p.s.i. |
| 1 hour diametral tensile strength | 4,317 p.s.i. |
| 7 day static creep | 0.05 percent |
| Dimensional Change | +0.1 percent |
| Gamma 2 presence | not detected |

EXAMPLE 7

An alloy containing by weight 46% silver, 23.95% copper, 28% tin, 2% indium and 0.05% platinum was made by the technique of Example 1. The obtained alloy was formed into an amalgam and tested as described in Example 1.

The results obtained were as follows:

| | |
|---|---|
| 30 minute compressive strength | 30,000 p.s.i. |
| 60 minute compressive strength | 48,500 p.s.i. |
| 24 hour compressive strength | 72,000 p.s.i. |
| 7 day compressive strength | 79,500 p.s.i. |
| 1 hour diametral tensile strength | 5,348 p.s.i. |
| 7 day static creep | 0.04 percent |
| Dimensional Change | +0.1 percent |
| Gamma 2 presence | not detected |

EXAMPLE 8

An alloy containing by weight 47% silver, 24% copper, 27.95% tin, 1% indium, 0.05% platinum was made by the technique of Example 1. The obtained alloy was formed into an amalgam and tested as described in Example 1.

The results obtained were as follows:

| | |
|---|---|
| 30 minute compressive strength | 34,000 p.s.i. |
| 60 minute compressive strength | 48,000 p.s.i. |
| 24 hour compressive strength | 72,000 p.s.i. |
| 7 day compressive strength | 79,000 p.s.i. |
| 1 hour diametral tensile strength | 5,100 p.s.i. |
| 7 day static creep | 0.04 percent |
| Dimensional Change | +0.03 percent |
| Gamma 2 presence | not detected |

EXAMPLE 9

An alloy containing by weight 46% silver, 24% copper, 28.95% tin, 1.0% indium and 0.05% platinum was made by the technique of Example 1. The obtained alloy was formed into an amalgam and tested as described in Example 1.

| | |
|---|---|
| 30 minute compressive strength | 36,000 p.s.i. |
| 60 minute compressive strength | 49,600 p.s.i. |
| 24 hour compressive strength | 72,000 p.s.i. |
| 7 day compressive strength | 79,000 p.s.i. |
| 1 hour diametral tensile strength | 5,200 p.s.i. |
| 7 day static creep | 0.04 percent |
| Dimensional Change | +0.03 percent |
| Gamma 2 presence | not detected |

EXAMPLE 10

An alloy containing by weight 46% silver, 24.3% copper, 28.65% tin, 1% indium and 0.05% platinum was made by the technique of Example 1. The obtained alloy was formed into an amalgam and tested as described in Example 1.

| | |
|---|---|
| 30 minute compressive strength | 38,500 p.s.i. |
| 60 minute compressive strength | 50,100 p.s.i. |
| 24 hour compressive strength | 73,000 p.s.i. |
| 7 day compressive strength | 79,500 p.s.i. |
| 1 hour diametral tensile strength | 5,350 p.s.i. |
| 7 day static creep | 0.03 percent |
| Dimensional change | +0.02 percent |
| Gamma 2 presence | not detected |

Once again, Examples 5 to 10 indicate that the best results are obtained with the use of small amounts of platinum in the range from about 0.05 to 0.1%.

Also, it appears that the combination of platinum with small amounts of indium enhances the improvement of properties compared to the degree of enhancement obtained with the addition of platinum and no indium.

Modifications and variations such as would be apparent to a skilled addressee are deemed within the scope of the present invention.

I claim:

1. A particulate dental amalgam alloy consisting of spherical particles formed of a dental amalgam alloy consisting essentially of, as alloying ingredients substantially uniformly distributed through each particle, from about 40 to 50% by weight silver, from about 20 to 30% by weight tin, from about 15 to 30% by weight copper, from 0 to about 1% by weight zinc and from about 0.03 to 0.5% by weight platinum, said particles having a particle size in the range from 1 to 55 microns with a majority of the particles being less than 35 microns in particle size.

2. A particulate dental amalgam alloy consisting of spherical particles formed of a dental amalgam alloy consisting essentially of, as alloying ingredients substantially uniformly distributed through each particle, from about 40 to 50% by weight silver, from about 20 to 30% by weight tin, from about 15 to 30% by weight copper, and from about 0.03 to 0.1% by weight platinum, said particles having a particle size in the range from 1 to 55 microns with a majority of the particles being less than 35 microns in particle size.

3. A particulate dental amalgam alloy as claimed in claim 2, amalgamated with mercury in a weight ratio of alloy to mercury of about 10:8.5 or less as a dental amalgam.

4. A particulate dental amalgam alloy according to claim 2, amalgamated with mercury in a weight ratio of alloy to mercury of about 10:8 or less to form a dental amalgam.

5. A particulate dental amalgam alloy according to claim 1, in which the majority of the particles have a particle size in the range from 5 to 30 microns.

* * * * *